United States Patent
Chen et al.

(10) Patent No.: US 10,888,616 B2
(45) Date of Patent: Jan. 12, 2021

(54) STABILIZED GLUCAGON SOLUTIONS

(71) Applicant: Latitude Pharmaceuticals, Inc., San Diego, CA (US)

(72) Inventors: Hailiang Chen, San Diego, CA (US); Andrew Xian Chen, San Diego, CA (US); Norman Keith Orida, San Diego, CA (US)

(73) Assignee: LATITUDE PHARMACEUTICALS, INC., San Diego, CA (US)

( * ) Notice: Subject to any disclaimer, the term of this patent is extended or adjusted under 35 U.S.C. 154(b) by 39 days.

(21) Appl. No.: 15/902,337

(22) Filed: Feb. 22, 2018

(65) Prior Publication Data

US 2018/0236079 A1  Aug. 23, 2018

Related U.S. Application Data

(63) Continuation of application No. PCT/US2016/050110, filed on Sep. 2, 2016.

(60) Provisional application No. 62/214,831, filed on Sep. 4, 2015.

(51) Int. Cl.

| A61K 47/10 | (2017.01) |
|---|---|
| A61K 9/08 | (2006.01) |
| A61K 38/26 | (2006.01) |
| A61K 47/02 | (2006.01) |
| A61K 9/00 | (2006.01) |
| A61K 47/20 | (2006.01) |
| A61K 47/18 | (2017.01) |
| A61K 47/26 | (2006.01) |
| A61P 3/08 | (2006.01) |
| A61K 47/12 | (2006.01) |

(52) U.S. Cl.
CPC ............ *A61K 47/10* (2013.01); *A61K 9/0019* (2013.01); *A61K 9/08* (2013.01); *A61K 38/26* (2013.01); *A61K 47/02* (2013.01); *A61K 47/12* (2013.01); *A61K 47/183* (2013.01); *A61K 47/20* (2013.01); *A61K 47/26* (2013.01); *A61P 3/08* (2018.01)

(58) Field of Classification Search
CPC ........ A61K 38/26; A61K 47/02; A61K 47/10; A61K 47/12; A61K 47/183; A61K 47/20; A61K 47/26; A61K 9/0019; A61K 9/08; A61P 3/08
See application file for complete search history.

(56) References Cited

U.S. PATENT DOCUMENTS

| 9,023,985 | B2 | 5/2015 | Jezek et al. | |
|---|---|---|---|---|
| 2011/0237510 | A1 | 9/2011 | Steiner et al. | |
| 2012/0046225 | A1 | 2/2012 | Prestrelski et al. | |
| 2013/0252893 | A1* | 9/2013 | Jezek ................... | A61K 47/186 514/11.7 |
| 2014/0378381 | A1 | 12/2014 | Chen et al. | |
| 2015/0291680 | A1 | 10/2015 | Ward et al. | |

FOREIGN PATENT DOCUMENTS

| EP | 2635296 | 9/2013 | |
|---|---|---|---|
| WO | 2006004696 | 1/2006 | |
| WO | 2009024797 | 2/2009 | |
| WO | WO-2009024797 A1 * | 2/2009 | ............ A61K 38/26 |
| WO | WO-2011011675 A1 * | 1/2011 | ........... A61K 9/0019 |
| WO | WO-2013101749 A1 * | 7/2013 | ............ A61K 38/26 |
| WO | 2016069409 | 5/2016 | |
| WO | 2017040928 | 3/2017 | |

OTHER PUBLICATIONS

ThermoFisher, Safety Data Sheet, Acetate Buffer, published online 2010.*
EP16843065.0, "Extended European Search Report," dated Feb. 25, 2019, 8 pages.
Acetate Buffer, pH 4.0 MSDS (ScienceLab.com, Inc.), section 2, May 21, 2013, 6 pages.
0.2M Acetate Buffer pH 5.0 Safety Data Sheet, Biochemical Diagnostics, Inc, section 3, Jun. 2015, 5 pages.
Acetate Buffer TS Material Safety Data Sheet, Spectrum Laboratory Products, Inc., section 2, Sep. 8, 2006, 7 pages.
International Search Report for parent PCT application PCT/US2016/050110, dated Dec. 5, 2016, 2 pages.
EP16843065.0, "Office Action," dated Mar. 30, 2020, 3 pages.

* cited by examiner

*Primary Examiner* — James H Alstrum-Acevedo
*Assistant Examiner* — Erinne R Dabkowski
(74) *Attorney, Agent, or Firm* — Kilpatrick Townsend & Stockton LLP

(57) ABSTRACT

This invention relates to ready-to-use and safe solution compositions of glucagon suitable for administration by manual injection or by an insulin pump or other injection device to treat hypoglycemia. Said compositions comprise glucagon, an acid, anti-gelling polyol, a stabilizing-salt, viscosity reducer and an antioxidant, have a final pH between about 2 and 5, and is gel-free, chemically-stable, and pump-able.

7 Claims, 5 Drawing Sheets

Specification includes a Sequence Listing.

SEQ ID NO: 1

STABILIZED GLUCAGON SOLUTIONS

CROSS-REFERENCE TO RELATED APPLICATIONS

This application is a continuation of International Application No. PCT/US2016/050110, filed Sep. 2, 2016 claims priority to U.S. Provisional Application No. 62/214,831, filed Sep. 4, 2015, the disclosures of which are hereby incorporated by reference in their entireties for all purposes.

REFERENCE TO A SEQUENCE LISTING

The Sequence Listing written in file SequenceListing_093108-1074137-000910US.txt created on Oct. 18, 2019, 657 bytes, machine format IBM-PC, MS-Windows operating system, is hereby incorporated by reference in its entirety for all purposes.

FIELD OF THE INVENTION

This invention relates to an injectable composition comprising glucagon, a polyol, an acid, water, an antioxidant, and a salt. Said composition is an aqueous solution that is clear, ready-to-use, non-gelling, stable and capable of providing fast-acting glucagon activity, and can be administered by a syringe or other injection devices such as an insulin pump for treatment and prevention of hypoglycemia and other diseases where glucagon is needed.

BACKGROUND OF THE INVENTION

Glucagon, a hormone secreted by the pancreas, is a polypeptide consisting of a single chain of 29 amino acids with a molecular weight of 3,485 Da. Medically, glucagon is used primarily to treat hypoglycemia (a condition of lower than normal blood glucose concentrations). Hypoglycemia is common in Type-1 diabetic patients and insulin users. Hypoglycemia causes anxiety, sweating, tremors, palpitations, nausea, and pallor, seizures, coma or even death in severe cases. Severe hypoglycemia is a life-threatening emergency that requires immediate medical intervention or rescue, for which the current standard of care is glucagon injection. Glucagon is also used during radiologic examinations of the stomach, duodenum, small bowel, and colon when diminished intestinal motility is required.

Upon injection, glucagon stimulates the liver to convert stored glycogen into glucose, which is released into the blood. For hypoglycemia rescue, the rapid elevation of blood glucose by glucagon is desired, preferably with the onset occurring within 5-20 minutes after injection. A glucagon formulation that is liquid, ready-to-use and/or ready-to-inject and is fast-acting is highly desired.

Glucagon has an isoelectric point of 7.1 and is insoluble in water at a physiological pH (pH 4-8). At pH 3 or lower, it is initially soluble, but will aggregate to form a gel within hours. The gelled glucagon consists predominantly of β-sheets or fibrils that are induced by the molecule's hydrophobicity and the inter- and intra-chain hydrogen bond forming potential of the peptide (Chou, P. Y., et al. 1975. Biochemistry 14(11):2536-2541). The gelled or aggregated glucagon is not suitable nor is it safe for injection. Thus, being non-gelling is also a desired property for a glucagon formulation in addition to being liquid, ready-to-use and fast-acting.

In addition to its gelling problem, glucagon undergoes various types of chemical degradation. In solution, glucagon rapidly degrades to form many degradation products. At least 16 degradation products of glucagon have been reported with the major degradation pathways being aspartic acid cleavage at positions 9, 15, and 21 and glutaminyl deamindation at positions 3, 20 and 24 (Kirsch, L. E., et al. 2000. International Journal of Pharmaceutics, 203:115-125). The chemical degradation of glucagon is rapid and complex. For example, in an acidic solution (pH 2-4), about 5-70% of glucagon breaks down into numerous degradation products within 24 hours at 37° C. (US Patent Application 2011/0097386). Preventing glucagon degradation in solution is very difficult and no effective method has been reported to inhibit glucagon degradation, especially the aspartic cleavage and glutaminyl deamindation of glucagon.

The two currently marketed glucagon drug products, GlucaGen Hypokit (glucagon hydrochloride) from Novo Nordisk A/S and Glucagon for Injection (rDNA Origin) from Eli Lilly and Company, are provided as two-part kits ("Glucagon Emergency Kit"). One part is a vial containing 1 mg (1 unit) of glucagon and lactose in a dry lyophilized solid mass ("cake") and the other part is a syringe containing a diluent comprising water, glycerin and hydrochloric acid. The cake provides a dry environment that keeps glucagon chemically stable. To use the Glucagon Emergency Kit, the diluent is first injected into the cake to dissolve it. The glucagon solution obtained is then drawn back into a syringe and then injected. The pH of this solution is approximately 2.0-3.5. The glucagon solution thus obtained is unstable and must be used immediately.

One must follow a multiple-step procedure to use the Glucagon Emergency Kit. This cumbersome procedure is difficult even for a normal person to perform. For someone incapacitated by hypoglycemia, self-administration of the kit can be extremely difficult or impossible. A delay in administering timely glucagon rescue therapy could result in death. Sadly, 6-10% of deaths of individuals with Type 1 diabetes are a result of hypoglycemia (Cryer, P. E. 2008. Diabetes 57(12): 3169-3176). Thus, a chemically-stable, ready-to-inject glucagon solution formulation is highly desirable for a lifesaving emergency hypoglycemia rescue application.

Insulin pumps have been widely used by insulin-dependent diabetics for over a decade. An insulin pump can be worn by a patient externally in close proximity to the body and deliver insulin via fine tubing through subcutaneously implanted needles. The subcutaneous needles may remain in place for up to a week.

Continuous glucose monitoring sensors or "CGM" capable of continuously reading blood glucose levels are used to provide blood glucose level information to the insulin pump to control insulin output in real time. However, when too much insulin has been pump-delivered, the current versions of the insulin pump do not have an effective means to counteract the drop in blood glucose and impending hypoglycemia from the already-administered insulin. In the normal individual, the body naturally counteracts rapid blood glucose decreases by secreting glucagon, but in a Type-1 diabetic patient, such function is impaired due to the diminished alpha cell activity.

A bi-hormonal or dual hormonal pump linked with CGM, capable of delivering both insulin and glucagon to the patient has the potential for better glucose control and functions like an artificial pancreas. When blood glucose reaches or is anticipated to reach hypoglycemic levels, the bi-hormonal pump delivers glucagon to counteract hypoglycemia. This capability allows the patient's blood glucose to be better regulated to within euglycemic levels, as performed by the pancreas of a non-Type-1 diabetic individual.

A bi-hormonal pump requires a liquid glucagon formulation that is ready-to-use, fast-acting, non-gelling and chemically-stable for at least three to seven days at body or near body temperature. This is because the pump is exposed to the patient body temperature and will be refilled with glucagon and insulin every half- or 1-week intervals. Furthermore, the glucagon formulation must be "pump-able", i.e., it can be delivered accurately and reliably in small volumes (e.g., 10-50 microliters) through thin infusion tubing by a pump. To be pump-able, the glucagon formulation must be non-gelling, have a low viscosity, and be compatible with an infusion set consisting of thin plastic tubing and fine catheters that deliver insulin/glucagon from the pump to the body.

Until there is a cure for Type-1 diabetes, a patient's use of a bi-hormonal pump could potentially last a lifetime. Therefore, the insulin and glucagon formulations used in a bi-hormonal pump must be held to very high safety standards due to the chronic exposure potential. The ingredients used in their formulations must have proven long-term safety records or be endogenous to the human body and used at safe levels to minimize toxicity during chronic use. A formulation containing ingredients that have not been previously approved by a regulatory agency (such as the FDA) for use in an injectable drug is certain to face serious regulatory scrutiny in proving its safety for marketing approval. The glucagon compositions disclosed herein contain only injectable ingredients that have previously approved for FDA for injection.

For use in both hypoglycemia rescue and in the bi-hormonal pump, a glucagon formulation must be fast-acting to and rapidly elevate blood glucose from hypoglycemic levels in a short time. The Glucagon Emergency Kit (Eli Lilly) is able to raise blood glucose concentration to a maximum (about 136 mg/dL) in humans within 26-30 minutes after a subcutaneous or intramuscular injection at the rescue dose (1 mg glucagon). This blood glucose concentration-versus-time relationship is also referred to as the pharmacodynamic profile for glucagon.

In summary, for hypoglycemia rescue, insulin pump or other indications utilizing glucagon, there is a need for a new formulation with the following properties:
 1. Liquid
 2. Ready-to-use, i.e., a liquid that can be injected directly
 3. Non-gelling
 4. Chemically-stable
 5. Pump-able
 6. Fast-acting, and
 7. Contains safe or FDA approved injectable ingredients.

To the best knowledge of this inventor, there is no glucagon solution composition in the prior art that is capable of meeting all seven of the above requirements.

WO 2013086292 A1 discloses glucagon formulations comprising glucagon, a bulking agent, and an acidifying agent in a pharmaceutically acceptable diluent. The composition can be readily lyophilized and rapidly reconstituted with its diluent. The bulking agents may include carbohydrates, amino acids, salts, mannitol, lactose, sucrose, dextran, sodium chloride, and combinations thereof. A bulking agent or matrix builder must be able to provide a solid structure or "cake" or powder after lyophilization and formulation must be glycerin-free. Mannitol is used in as a bulking agent at a concentration from approximately 1.0% to approximately 10.0% (w/v). The composition disclosed is provided in 2 chambers and is not a ready-to-use or liquid formulation.

WO2012059764 teaches aqueous compositions having a pH between 4 and 7 comprising glucagon and a cationic surfactant as solubilising agent. Examples of cationic surfactants include benzethonium salts, benzalkonium salts, and cetyl trimethylammonium salts. Cationic surfactants are toxic and are not safe for the long-term chronic use as would be utilized in the insulin/glucagon pump.

WO 2011049713 claims a formulation composed of a sugar and a surfactant, wherein "sugar" refers to a monosaccharide or disaccharide with preferred examples including sucrose, maltose and glucose. A surfactant can be an amphophilic surfactant such as phospholipids or giycerophospholipids with preferred embodiment of myristoyl lysophosphocholine (LMPC). A anti-gelling agents can also be added such as ethanol added up to 10%, most preferably at 2% v/v, to prevent gelation. Other examples of alcohols that inhibit gelation include monohydric alcohols such as pentanol (amyl alcohol) and hexadecane-1-ol (cetyl alcohol, palmityl alcohol). Polyhydric alcohols, such as propane 1,2,3,triol (glycerin), butane 1,2,3,4-tetraol (erythritol), Pentane-1,2,3,4,5,6-hexol (marmitol, sorbitol) and heptanes-1, 2,3,4,5,6,7-heptol (volemitol); unsaturated aliphatic alcohols such as 3,7-dimethylocta-2,6~dien-1~ol (Geraniol); and alicyclic alcohols such as cyclohexane-1,2,3,4,5,6-geksol (inositol) and 2-(2-propyl)-5-methyl-cyclohexane-1-ol (menthol). No working concentration range is provided for these alcohols. The disclosed surfactants (e.g., LMPC) or alcohols (e.g., pentanol) have not been approved by the FDA for injection and are unsafe for the insulin/glucagon pump use.

US20120232001 claims a stable formulation comprising: (a) a peptide or a salt thereof, wherein the peptide has been dried in a non-volatile buffer, and wherein the dried peptide has a pH memory that is about equal to the pH of the peptide in the non-volatile buffer; and (b) an aprotic polar solvent; wherein the moisture content of the formulation is less than 5%, and wherein the dried peptide maintains the pH memory that is about equal to the pH of the peptide in the non-volatile buffer when the dried peptide is reconstituted in the aprotic polar solvent. Examples of aprotic polar solvents include dimethylsulfoxide (DMSO), dimethylformamide (DMF), ethyl acetate, n-methyl pyrrolidone (NMP), dimethylacetamide (DMA), and propylene carbonate. The disclosed aprotic solvent (e.g. DMSO) has been reported to cause injection site reactions (Haymond, M W, Redondo, M J, et al. 2016. Nonaqueous, mini-dose glucagon for treatment of mild hypoglycemia in adults with Type 1 diabetes: A dose seeking study. Diabetes Care 39: 465-468) and is unsafe for the insulin/glucagon pump use.

WO1995032730 discloses a pharmaceutical preparation comprising glucagon and a stabilizing amount of a pharmaceutically acceptable ampholyte except histidine. The ampholyte is an amino acid (except histidine), or a derivative of glycine, N-methylglycine (sarcosine), tri-methylglycine hydroxide inner salt (betaine), alanine, β-alanine, valine, leucine, nor-leucine, isoleucine, serine, threonine, aspartic acid, glutamic acid, hydroxyglutamic acid, lysine, hydroxylysine, ornithine, arginine, methionine, asparagine and glutamine, a dipeptide such as glycylglycine, a sulfonic acid or a derivative such as taurine; creatinine, or ethylenediamine-tetraacetic acid (EDTA). For each milligram of glucagon, the amount of stabilizing amino acid or dipeptide present is 0.1 to 50 micromoles, which corresponds 0.0075 to 3.75 mg/mL for glycine. The inventors of this application were not able to stabilize glucagon using ingredients disclosed by WO1995032730.

EP1687019A2 discloses a pharmaceutical formulation comprising at least one peptide and propylene glycol, wherein said propylene glycol is present in said formulation in a final concentration of from about 1 mg/ml to about 100 mg/ml and wherein said formulation has a pH of from about 7.0 to about 10.0. No example of any composition containing glucagon or any teaching of the desired properties for a glucagon formulation or methods to obtain these properties is provided in EP1687019A2.

None of the above disclosed compositions can meet all of the following requirements desired for a new glucagon formulation:
1. Liquid
2. Ready-to-use
3. Non-gelling
4. Chemically-stable
5. Pump-able
6. Fast-acting, and
7. Contains safe ingredients.

SUMMARY OF THE INVENTION

This invention relates to new glucagon formulation with the following properties:
1. Liquid
2. Ready-to-use
3. Non-gelling
4. Chemically-stable
5. Pump-able
6. Fast-acting, and
7. Contains safe ingredients.

This invention first relates to a finding that a non-gelling solution composition of glucagon can be obtained by a combination of a polyol and an acid.

This invention also relates to a finding that such a non-gelling solution composition of glucagon can be obtained without containing a surfactant, sugar, aprotic solvent, phospholipids, lysophospholipid or ampholyte.

This invention further relates to a surprising finding that a non-gelling and chemically-stable composition of glucagon can be obtained by adding a stabilizing-salt and an antioxidant to the non-gelling composition comprising a combination of a polyol and an acid.

This invention relates to yet another surprising finding that a non-gelling, chemically-stable and pump-able composition of glucagon can be obtained by adding a viscosity-reducer to the non-gelling and chemically-stable composition comprising a combination of a polysol, an acid, a stabilizing-salt and an antioxidant.

DETAILED DESCRIPTION OF THE INVENTION

I. Definitions

Figure 1:
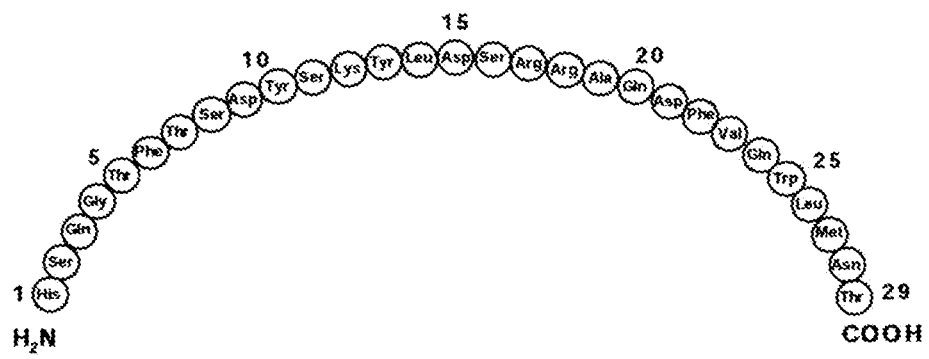
FIG. 1—shows the amino acid sequence of glucagon (SEQ ID NO: 1).

As used herein, the various terms shall have the following definitions:

As used herein, "about" describes a quantity with a range covering 10% expansion from both sides of the target value. For example, "about 100" means any value between 90 and 110 including 90 and 110.

As used herein, an "acid" refers to any organic or inorganic acid that is suitable for injection or injectable acid. The injectable acids are acids that have previously approved by the FDA for use in injectable drugs and are identified on the FDA's Inactive Ingredient List. Acids that are particularly useful for this invention include, but are not limited to, acetic acid, ascorbic acid, aspartic acid, benzenesulfonic, benzoic acid, citric acid, formic acid, fumaric acid, hydrochloric acid, hydrobromic acid, lactic acid, lactobionic acid, maleic acid, malic acid, malonic acid, methanesulfonic acid, phosphoric acid, propionic acid, succinic acid, sulfuric acid, and tartaric acid. The preferred acids are those having a pKa less than 5. The more preferred acids are citric acid, hydrochloric acid, lactic acid, methanesulfonic acid, phosphoric acid, propionic acid, sulfuric acid, and tartaric acid.

As used herein, an "alcohol" is an organic compound in which a single hydroxyl functional group (—OH) is bound to a carbon atom and this carbon is saturated, having single bonds to three other atoms. The preferred alcohol for the composition of this invention is ethanol. Ethanol alone is not a good solvent for glucagon and is not safe to inject at a high concentration because it causes irritation or pain at the injection site. Ethanol does not have the same anti-gelling property as a polyol and cannot substitute for the polyol in a composition of the present invention. Ethanol can, however, be added to a composition of this invention to a low concentration to reduce viscosity of the composition to improve injectability or pump-ability.

As used herein, the phrase "anti-gelling" refers to the ability of certain agent to prevent glucagon gelation, aggregation or fibril-formation.

As used herein, "antimicrobial preservative" is a pharmaceutical additive that can be added to a liquid composition to inhibit the growth of bacteria and fungi. The antimicrobial preservatives useful in the present invention include, but are not limited to, cresols, phenol, benzyl alcohol, ethanol, chlorobutanol, parabens, imidura, benzylkonium chloride, EDTA or its salt or a combination thereof.

An "antioxidant" is a pharmaceutical additive that can be added to a liquid composition to prevent oxidation of the active drug or an inactive component. Antioxidants include reducing agents, metal ion chelating agents and inert gases.

"Arrhenius' equation" is a formula for the temperature dependence of reaction rates. Arrhenius' equation gives the dependence of the rate constant k of a chemical reaction on the absolute temperature T(in kelvin), where A is the preexponential factor (or simply the prefactor), $E_\alpha$ is the activation energy, and R is the Universal gas constant.

$$k = Ae^{-E_\alpha/(RT)}$$

Historically, Arrhenius' equation is used to predict the reaction rate at a lower temperature using the reaction rate data collected at higher temperatures.

As used herein, "body or near body temperature" is about 30° to 40° C.

As used herein, "chemically-stable" means the composition retains no less than 65% of the initial glucagon concentration after 3-7 days at the body temperature, or after storage for 24 months at 2-8° C. or after storage for 12 months at 25° C.

As used herein, "detergents" are water-soluble surfactants that can be used to dissolve and clean oily substances with water.

As used herein, the phrase "fast-acting" means a glucagon composition is able to elevate blood glucose levels to more than 100 mg/dl within 30 minutes, preferably within 20 minutes and more preferably within 10 minutes in a mammal after administering the composition containing a dose that is equivalent to the 1 mg adult human dose by a subcutaneous or intramuscular injection.

As used herein, "FDA" refers to the US Food and Drug Administration.

As used herein, "filterable" means the ability of a liquid to pass through a filter membrane of a certain pore size such as 0.2-microns without a significant loss (5% or more) of glucagon.

As used herein, the term "fine needle" includes a small-diameter, hollow hypodermic needle that is used with a syringe or pump for subcutaneous, intravenous, or other type of injection. The outer diameter of the needle is indicated by the needle gauge system. According to the Stubs Needle Gauge system, hypodermic needles in common medical use range from 7 (the largest) to 33 gauge (G)(the smallest). As used herein, "fine needle" therefore includes needles ranging from 21 to 33G, preferably 25G to 31G and most preferably 27G to 31G.

As used herein, the phrase "gel-free" means a glucagon composition that exhibits no visible glucagon precipitates, particles, fibrils or gelation or means that the glucagon composition passes the dye binding test as described in Example 3.

As used herein, "glucagon" refers to the full length peptide, glucagon, having the empirical formula of $C_{153}H_{225}N_{43}O_{49}S$, a molecular weight of 3,483 Da., and composed of a single-chain polypeptide containing 29 amino acid residues, with the amino acid sequence shown in FIG. 1, or any other peptide that contains a glucagon-like sequence or share the same gelling or chemical degradation problems as glucagon.

As used herein, "glucagon fibril" means aggregated glucagon that presents in particles or fiber-like structures. Glucagon fibrils can be detected visually or quantitated by certain analytical methods such as particle size analysis or dye-binding analysis as described in Example 3.

As used herein, "GRAS" is an acronym for the phrase Generally Recognized As Safe, as defined in the 1958 Food Additives Amendment to the Federal Food Drug and Cosmetic Act ("FD&C Act") to exempt certain food ingredients from the definition of food additive.

As used herein, an "insulin pump" is a medical device used for the administration of insulin in the treatment of diabetes mellitus, also known as continuous subcutaneous insulin infusion therapy. The device includes the pump (including controls, processing module, and batteries), a disposable reservoir for insulin (inside the pump), a disposable infusion set, including a cannula for subcutaneous insertion (under the skin) and a tubing system to interface the insulin reservoir to the cannula. An insulin pump may also deliver a second solution such as a glucagon composition to prevent insulin overdose or hypoglycemia. An insulin pump capable of delivering two solutions is also referred to as a bi-hormonal pump.

As used herein, "medium chain triglycerides" ("MCTs") are medium-chain (6 to 12 carbons) fatty acid esters of glycerol. An MCT can be either derived from a natural source or made synthetically.

The term "metal ion chelating agent or chelator" includes metal ion chelators that are safe to use in an injectable product. A metal ion chelator works by binding to a metal ion and thereby reduces the catalytic effect of that metal ion on the oxidation, hydrolysis or other degradation reactions. Metal chelators that are useful in this invention may include ethylenediaminetetraacetic acid (EDTA, edetate), glycine and citric acid and the respective salts or a mixture thereof. Examples of the preferred chelators include sodium, potassium or calcium salts of EDTA.

As used herein, "pH" is the pH readout of the composition of the present invention by a typical pH meter consists of a glass electrode connected to an electronic meter that measures and displays the pH. The pH meter was calibrated using aqueous standard pH buffers.

As used herein, a "polyol" is an alcohol molecule having multiple hydroxyl groups. The preferred polyols for this invention include propylene glycol, glycerin (glycerol), polyethylene glycol (PEG) and sugar alcohols. Sugar alcohols are a class of polyols that includes mannitol, maltitol, sorbitol, xylitol, erythritol, and isomalt. The sugar alcohols are usually formed under mild reducing conditions from their analogue sugars. A lower MW polyol (e.g., propylene glycol, glycerin) is preferred over a higher MW polyol (e.g., polyethylene glycol) for lower viscosity and better anti-gelling property for a glucagon composition. The more preferred polyols are propylene glycol, glycerin and low MW polyethylene glycol (e.g., PEG200, PEG300 and PEG400). The most preferred polyol is propylene glycol. Propylene glycol has been approved by the FDA for use in drugs administered by subcutaneous, intramuscular or intravenous injection according to the FDA's Inactive Ingredient List.

As used herein, the phrase "non-gelling" means a glucagon composition remains gel-free after 3-7 days at body temperature, OR after storage under a stressing condition that is equivalent to 24 months at 5° C., OR after storage under a stressing condition that is equivalent to 12 months at 25° C.

As used herein, the phrase "pump-able" means that a solution can be delivered by an insulin pump with delivery volume accuracy within 80 to 120% AND the solution is free of any strong solvent such as DMSO, NMP or other aprotic solvent that can dissolve or cause damage to the plastic parts in the pump or infusion set used with the insulin pump.

As used herein, the phrase "safe ingredient" refers to an excipient that has been approved by the FDA (at the time of this application) for use in an injectable drug. The safe ingredients are listed on the FDA's Inactive Ingredient List.

As used herein, the phrase "stabilizing-salt" refers to a salt that is able to increase the chemical stability of glucagon in a non-gelling composition of the present invention. The stability of glucagon is primarily quantitated using the glucagon USP ASSAY method.

As used herein, the term "substantially free" means less than 1% of the total composition weight.

As used herein, a "sugar" refers to a carbohydrate additive(s) that is normally added to a liquid composition to adjust osmotic pressure or tonicity.

As used herein, "solution" refers to a clear, homogeneous liquid composed of only one phase.

As used herein, "surfactants" refers to compounds that lower the surface tension of a liquid or the interfacial tension between two liquids.

As used herein, "USP" means the current edition of the United State Pharmacopeia.

As used herein, the phrase "viscosity-reducer" refers to a liquid that is capable of reduce viscosity of the non-gelling and chemically-stable composition of the current invention. A viscosity-reducer is necessary for a pump-able composition of glucagon. Examples of useful viscosity-reducer for the present invention include, but are not limited to ethanol, medium chain triglycerides and ethyl oleate, or a mixture thereof.

As used herein, the term "%" means the weight by volume percentage, or % w/v. For example, 1% means one gram in 100 mL or 10 mg/mL.

As used herein, the term "% w/w" means the weight by weight percentage, or % w/w. For example, 1% w/w means one gram in 100 g or 10 mg/g.

II. Description

Other than water, polyols are the most suitable solvents for injection because they are either endogenous to human body (e.g., glycerin) or are generally recognized as safe (GRAS). Polyols such as propylene glycol (PG), glycerin, sorbitol, polyethylene glycol have been approved by the FDA for use in injectable drugs. As a vehicle for a new glucagon formulation, a polyol is preferred over other organic solvents such as DMSO due to its long history of safe use as an injectable excipient. This invention relates to a glucagon solution composition comprising a polyol.

Glucagon is insoluble in pure water or alcohol. The Glucagon Emergency Kits marketed by Eli Lilly and Co. or Novo Nordisk A/S uses an acid (HCl) to help dissolve glucagon in water (but such a solution quickly forms a gel over time). Similarly, this inventor discovered that a combination of an acid and a polyol could also dissolve glucagon but forms a non-gelling solution.

However, the glucagon in such a non-gelling solution comprising an acid-polyol combination is not chemically-stable. Subsequently, this inventor discovered that adding an anti-oxidant and a stabilizing-salt to the non-gelling solution comprising an acid-polyol combination surprisingly improves the glucagon chemical stability in the solution, resulting in a non-gelling AND chemically-stable solution composition for glucagon.

The effects of the various formulation components on glucagon gelation and chemical stability are summarized in the table below:

| Component | Gelation | Chemical stability |
|---|---|---|
| Water | Yes | Poor |
| Alcohol (e.g. ethanol) | Yes | Poor |
| Polyol (e.g. glycerin) | Yes | Poor |
| Water + Acid | Yes | Poor |
| Alcohol + Acid | Yes | Poor |

-continued

| Component | Gelation | Chemical stability |
|---|---|---|
| Polyol + Acid | No | Poor |
| Water + Polyol + Acid | No | Poor |
| Water + Polyol + Acid | No | Poor |
| Water + Polyol + Acid + antioxidant | No | Better |
| Water + Polyol + Acid + antioxidant + stablizing-salt | No | Best |
| Polyol + Acid + antioxidant + stablizing-salt | No | Best |
| Water + Polyol + Acid + antioxidant + stablizing-salt + Viscosity reducer | No | Best |
| Polyol + Acid + antioxidant + stablizing-salt + Viscosity reducer | No | Best |

Therefore, a polyol identified and added for the above purposes is referred to as an "anti-gelling polyol" and the salt as a "stabilizing-salt". The mechanism of the anti-gelling polyol or stabilizing-salt is unknown and is not found in any prior art.

III. Embodiments

In one embodiment, this invention provides a non-gelling composition comprising glucagon, an anti-gelling polyol, and an acid, wherein said composition has a pH of from about 2 to about 5.

In another embodiment, this invention provides a non-gelling and chemically-stable composition comprising glucagon, an anti-gelling polyol, an acid and a stabilizing-salt, wherein said composition has a pH of from about 2 to about 5.

In yet another embodiment, this invention provides a non-gelling, chemically-stable and pump-able composition comprising glucagon, an anti-gelling polyol, an acid, a stabilizing-salt, and a viscosity-reducer, wherein said composition has a pH of from about 2 to about 5.

In one embodiment, the glucagon in the formulation is made by chemical synthesis or DNA recombinant technology or derived from an animal source.

In a preferred embodiment, glucagon is made by chemical synthesis or DNA recombinant technology.

In one embodiment, the anti-gelling polyol is selected from a group consisting of propylene glycol, glycerol (or glycerin), sorbitol and polyethylene glycol and a mixture thereof.

In a preferred embodiment, the anti-gelling polyol is propylene glycol, glycerin or a combination thereof.

In one embodiment, the stabilizing-salt is selected from a group consisting of salts formed by ammonium, calcium, magnesium, potassium, sodium or zinc cation with a counter ion of acetate, benzoate, bisulfite, bicarbonate, carbonate, citrate, lactate, metabisulfite, phosphate, sulfate, sulfite or tartrate, or a combination thereof.

In a preferred embodiment, the stabilizing-salt is sodium chloride, sodium acetate and calcium chloride.

In one embodiment, the viscosity-reducer is selected from a group consisting of ethanol, ethyl oleate or a medium chain triglyceride or a combination thereof.

In a preferred embodiment, the viscosity-reducer is ethanol.

In one embodiment, the acid is selected from the group consisting of hydrochloric acid, sulfuric acid, acetic acid, citric acid, phosphoric acid, lactic acid, tartaric acid, or methanesulfonic acid.

In a preferred embodiment, the acid is selected from the group consisting of hydrochloric acid, sulfuric acid, lactic acid and tartaric acid.

In one embodiment, the composition of this invention further contains an antioxidant.

In a preferred embodiment, the antioxidant is selected from a group comprising methionine, cysteine, dextrose, fructose, lactose, and EDTA or a salt of edetate (EDTA), or combination thereof.

In a more preferred embodiment, the antioxidant is a combination of methionine and EDTA.

In one embodiment, the composition of this invention contains water.

In another embodiment, the composition of this invention is substantially free of water.

In one embodiment, each milliliter of the composition of this invention contains 0.1 to 5 mg of glucagon.

In a preferred embodiment, each milliliter of the composition of this invention contains 0.5 to 3 mg of glucagon.

In a more preferred embodiment, each milliliter of the composition of this invention contains about 1 mg of glucagon.

In yet another preferred embodiment, each milliliter of the composition of this invention contains 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 and 3.0 mg of glucagon.

In one embodiment, the anti-gelling polyol is present in a final concentration from about 40% to 97%.

In a preferred embodiment, the anti-gelling polyol is present in a final concentration from about 75% to about 85%.

In a more preferred embodiment, the anti-gelling polyol is present in a final concentration of about 60% to about 80%.

In another embodiment, the anti-gelling polyol is present in a final concentration of about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90%.

In one embodiment, the water is present in a final concentration from about 1% to 20%.

In a preferred embodiment, the water is present in a final concentration from about 3% to 5%.

In a more preferred embodiment, the water is present in a final concentration of about 4%.

In another embodiment, the water is present in a final concentration of about 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0%.

In one embodiment, the stabilizing-salt is present in a final concentration from about 0.1% to 3%.

In a preferred embodiment, the stabilizing-salt is present in a final concentration from about 0.5% to 3%.

In a more preferred embodiment, the stabilizing-salt is present in a final concentration from about 1%.

In another embodiment, the stabilizing-salt is present in a final concentration of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0%.

In one embodiment, the viscosity-reducer is present in a final concentration from 2% to 20%.

In a preferred embodiment, the viscosity-reducer is present in a final concentration from 12% to 18%.

In a more preferred embodiment, the viscosity-reducer is present in a final concentration of about 15%.

In another embodiment, the viscosity-reducer is present in a final concentration of about 5, 6, 7, 8, 9, 10, 11, 12, 13, 14, 15, 16, 17, 18, 19, or 20%.

In one embodiment, the antioxidant is present in a final concentration of about 0.1 to 1% for methionine and 0.001% to 0.1% for EDTA.

In a more preferred embodiment, the antioxidant is present in a final concentration of about 0.1% to 0.5% for methionine and about 0.05% to 1% for EDTA.

In another embodiment, the antioxidant is present in a final concentration of about 0.15% for methionine and about 0.015% for EDTA.

In one embodiment, a sufficient amount of acid is added to the composition to achieve the composition pH.

In one embodiment, the composition contains about 50 to 250 mM acid. The actual amount of acid may vary depending upon the type of acid, concentration of glucagon or stabilizing-salt used, as long as a sufficient amount is added to achieve the composition pH.

In one embodiment, the composition of this invention has a pH of from about 2 to about 5.

In a preferred embodiment, the composition of this invention has a pH of from about 2.8 to about 4.2.

In a more preferred embodiment, the composition of this invention has a pH of about 3.4.

In another embodiment, the composition of this invention has a pH of 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4 or 4.5.

In one embodiment, this invention provides a solution composition comprising about 0.1 to 3 mg/mL glucagon, about 80% to 98% propylene glycol, about 0% to 20% water and sufficient hydrochloric acid to adjust composition pH to from about 2 to 5.

In one embodiment, this invention provides a solution composition comprising about 0.1 to 3 mg/mL glucagon, about 80% to 98% glycerin, about 0% to 20% water and sufficient hydrochloric acid to adjust composition pH to from about 2 to 5.

In one embodiment, this invention provides a solution composition comprising about 0.1 to 2 mg/mL glucagon, about 60% to 80% propylene glycol, about 10% to 30% glycerin, about 2% to 6% water and sufficient hydrochloric acid to adjust composition pH to from about 3 to 4.5.

In one embodiment, this invention provides a solution composition comprising about 0.1 to 2 mg/mL glucagon, 60% to 80% propylene glycol, 10% to 30% glycerin, about 2% to 6% water, about 0.5% to 1.5% sodium chloride, and sufficient hydrochloric acid to adjust composition pH to from about 3.5 to 4.5.

In one embodiment, this invention provides a solution composition comprising about 0.1 to 2 mg/mL glucagon, 60% to 80% propylene glycol, 10% to 30% glycerin, about 2% to 6% water, about 0.5% to 1.5% sodium acetate, and sufficient hydrochloric acid to adjust composition pH to from about 3.5 to 4.5.

In one embodiment, this invention provides a solution composition comprising about 0.1 to 2 mg/mL glucagon, 60% to 80% propylene glycol, 10% to 30% glycerin, about 2% to 6% water, about 0.5% to 1.5% calcium chloride, and sufficient hydrochloric acid to adjust composition pH to from about 3.5 to 4.5.

In a preferred embodiment, this invention provides a solution composition comprising about 1 mg/mL glucagon, about 80% propylene glycol, about 4% water, about 1% sodium chloride, and sufficient hydrochloric acid to adjust composition pH to from about 3.5 to 4.5.

In a more preferred embodiment, this invention provides a solution composition comprising about 1 mg/mL glucagon, about 65% propylene glycol, about 15% ethanol, about 4% water, about 1% sodium chloride, about 0.15% methionine, about 0.015% EDTA disodium dihydrate, and sufficient hydrochloric acid to adjust composition pH to from about 3.5 to 4.5.

In one embodiment, the composition of this invention remains gel-free after storage at body temperature (30-40° C.) for 3-7 days.

In another embodiment, the composition of this invention remains gel-free after storage under a stressing condition that is equivalent to 24 months at 5° C.

In a preferred embodiment, the composition of this invention remains gel-free after storage under a stressing condition that is equivalent to 12 months at 25° C.

In one embodiment, the composition of this invention retains no less than 65% of its initial glucagon concentration after storage at body temperature (30-40° C.) for 3-7 days.

In another embodiment, the composition of this invention retains no less than 65% of its initial glucagon concentration after storage under a stressing condition that is equivalent to 24 months at 5° C. The 65% acceptance limit is defined by the United States Pharmacopeia Glucagon for Injection Monograph (USP-NF 36). The stressing condition is equivalent to 24 months at 5° C., based on an Arrhenius calculation (Example 7).

In a preferred embodiment, the composition of this invention retains no less than 65% of its initial glucagon concentration after storage under a stressing condition that is equivalent to 12 months at 25° C. The 65% acceptance limit is defined by the United States Pharmacopeia Glucagon for Injection Monograph (USP-NF 36) and the stressing condition equivalent to 12 months at 25° C., based on an Arrhenius calculation (Example 7).

In one embodiment, composition of this invention has a viscosity of no more than 50 centipoise at room temperature.

In a preferred embodiment, composition of this invention is pump-able.

In a preferred embodiment, the composition of this invention is ready-to-use.

In one embodiment, the composition of this invention is fast-acting.

In a preferred embodiment, the composition of this invention is able to elevate blood glucose level to more than 100 mg/dl within 30 minutes in an animal after receiving a dose that is equivalent to the 1 mg adult human dose by a subcutaneous or intramuscular injection.

In one embodiment, the composition of this invention is administered by a syringe or insulin pump or other injection device.

In one embodiment, the composition of this invention is filterable.

In one embodiment, the composition of this invention comprises safe ingredients.

In a preferred embodiment, the composition of this invention comprises only ingredients that have been approved by the FDA for use in injectable drugs.

In one embodiment, the composition of this invention is used to treat or prevent hypoglycemia.

IV. Methods of Making

In one embodiment, the present invention provides a method for preparing a solution composition comprising glucagon, said method comprising:
Step 1. Combine and mix the polyol, anti-oxidant, stabilizing-salt, viscosity-reducer (optional) and water (optional) to form a vehicle;
Step 2. Adjust pH of the vehicle;
Step 3. Add glucagon to the vehicle and mix to dissolve;
Step 4. Adjust pH as needed to the final target pH to obtain the final solution;
Step 5. Pass the final solution through a 0.2-micron filter to sterilize; and
Step 6. Fill the filtered solution into vials or syringes.

In a certain embodiment, the order of the above steps is altered or combined or additional steps are added as long as the final solution is clear and at the targeted pH.

In a certain embodiment, the order of addition or mixing methods is altered as long as the final solution is clear and filterable.

V. Methods of Use

In one embodiment, the composition of the present invention is a liquid filled into a glass vial or ampule. The liquid is drawn into a syringe prior to use.

In a preferred embodiment, the composition of the present invention is provided in a pre-filled syringe or other injection device with attached hypodermic needle and is ready to inject. This feature is particularly desirable for emergency hypoglycemia rescue. A typical adult dose used to reverse severe hypoglycemia is 1 mg glucagon.

In a certain embodiment, the composition of the present invention is administered via an intravenous, intramuscular or subcutaneous injection.

In another preferred embodiment, the composition of the present invention is filled in a cartridge (reservoir) or a vial and fitted to an insulin pump and its liquid content is delivered through an infusion set. To use glucagon by pump delivery, the pump cartridges (obtained prefilled from a manufacturer or self-filled by the end user) are loaded into the pump device. At the end of term of use (e.g., 3-7 days), the remaining glucagon solution is discarded and fresh glucagon solution is provided to the pump. The dose of glucagon delivered by the pump will be determined by the needs of the patient. In studies of a prototype insulin-glucagon bi-hormonal pump, the amount of glucagon used to achieve blood glucose control over a 24 hr period was reported to be 0.120 to 0.377 mg for an adult (El-Khatib, F. et al. 2010. Science Transl. Med. 2:27ra27).

In another preferred embodiment, the composition of the present invention contains an antimicrobial preservative and is filled into a vial or injection device (i.e., a pre-filled syringe or a vial in an autoinjector, among other configurations). The vial/syringe contains sufficient quantity for multiple doses and said content may be dosed to patients in multiple injections. Each time, a small and varying volume of the content is injected. This multiple-dose and variable dose feature would be particularly desirable for certain radiology procedures to inhibit gastrointestinal motility during radiology examination, for which a lower dose of glucagon is used. The addition of the antimicrobial preservative in the solution prevents potential microbial growth after multiple punctures of the vial to remove multiple small doses or multiple injections using the same prefilled syringe. An antimicrobial preservative is also desirable for the bi-hormonal pump application, which could expose the solution to body temperature for several days.

The present invention will be further understood by reference to the following non-limiting examples.

Example 1 Comparison of Glucagon Gelation in Water and in Polyols

The aim of this study was to compare the effect of solvent on glucagon gelation. For each test composition, the intended components were combined and mixed to form a vehicle, to which glucagon was added to achieve a 1 mg/mL concentration. To some vehicles, an acid (HCl) was added. The final pH was recorded for each composition. The appearance of each composition was recorded immediately after preparation (Initial) and after 10 days of storage at room temperature. The results are shown in TABLE 1.

TABLE 1

Gelation of glucagon in solution

| Component | Final pH | Appearance Initial | RT for 10 days |
|---|---|---|---|
| $H_2O$ | 4.7 | Precipitates | Gel |
| Ethanol | Not tested | Precipitates | Precipitates |
| $H_2O$ + HCl | 3.2 | No gel | Gel |
| 10% $H_2O$ + propylene glycol + HCl | 3.2 | No gel | No gel |
| 10% $H_2O$ + glycerin + HCl | 3.2 | No gel | No gel |
| 10% $H_2O$ + ethanol + HCl | 3.2 | No gel | Precipitate |
| Propylene glycol + HCl | 3.2 | No gel | No Gel |
| PEG200 + HCl | 3.2 | No gel | No Gel |
| Sorbitol + HCl | 3.2 | No gel | No Gel |

Example 2 Effect of pH on Glucagon Gelation in Water and Polyol

The aim of this study was to compare effect of pH on glucagon gelation in two solvents (water or propylene glycol (PG)) at 2 mg/mL. To prepare the test compositions, glucagon powder was initially suspended in water or propylene glycol. The suspension was divided into 5 portions and pH of each portion was adjusted using HCl to the final pH. The appearance of each composition was recorded after being agitated at RT for 16 h and after 10 days of storage at room temperature. The results are shown in TABLE 2.

TABLE 2

Glucagon gelation in solution at different pH in water or PG at 2 mg/mL

| Solvent | pH | Appearance Agitated at RT for 16 h | Stored at RT for 10 days |
|---|---|---|---|
| $H_2O$ | 2.8 | No gel | Gel |
|  | 3.3 | No gel | Gel |
|  | 3.9 | No gel | Gel |
|  | 4.4 | No gel | Gel |
|  | 6.1 | Gel | Gel |
| PG | 1.2 | No gel | No gel |
|  | 2.4 | No gel | No gel |
|  | 3.5 | No gel | No gel |
|  | 5.2 | No gel | No gel |
|  | 6.9 | No gel | No gel |

Example 3 Detection of Glucagon Gel or Fibril in Formulations Using Thioflavin T Fluorescent Dye Binding Test The aim of this test was to detect glucagon gels or fibrils in formulations using thioflavin T (ThT) fluorescent dye binding. Detection is achieved by using dual wavelength measurements, one for the internal standard 8-anilino-1-naphthalenesulfonic acid hemi magnesium salt hydrate (ANSA) and one for ThT-glucagon bound material. ThT is a dye that fluoresces upon interaction with the beta-sheet structures that comprise glucagon gel or fibrils. Each test solution was measured for fluorescence after four hours of quiescent room temperature incubation. The method is intended to assess the gel-forming propensity in the test formulations.

A solution composition of the present invention (F-618) in this test contained 0.1% glucagon, 30% glycerin, 2% calcium chloride 0.15% L-methionine, 0.015% EDTA disodium dehydrate, 4% water, about 48.8% propylene glycol and HCl to adjust the pH to 3.4. For comparison, the Glucagon Emergency Kit (Eli Lilly) was also tested.

The test results (below) indicate that solution prepared from the Glucagon Emergency Kit formed gels after 7 days at 37° C., while F-618 remained gel-free under the same conditions and also after being stored at 40° C. for 21 days or at 60° C. for 15 days.

TABLE 3

Detection of Glucagon Fibrillation by ThT Dye Binding Assay

| Sample ID | Gel Detected |
|---|---|
| Glucagon at 3 mg/mL in water at pH 2.8, RT for 4 hr ("Positive Control") | Yes |
| Glucagon Emergency Kit, fresh reconstituted | No |
| Glucagon Emergency Kit, agitated for 3 days at 37° C. | No |
| Glucagon Emergency Kit, agitated for 7 days at 37° C. | Yes |
| F-618, agitated for 3 days at 37° C. | No |
| F-618, agitated for 7 days at 37° C. | No |
| F-618, stored for 21 days at 40° C. | No |
| F-618, stored for 15 days at 60° C. | No |

Example 4 Preparation of Glucagon Solution Compositions of Present Invention

The compositions of several typical glucagon solution formulations based on this invention are provided in TABLE 3.

TABLE 3

Glucagon Solution Formulation Compositions (% w/w)

| Component | F-573 | F-575 | F-590 | F-609 | F-618 | F-621 | F-648 |
|---|---|---|---|---|---|---|---|
| Glucagon | 0.1 | 0.1 | 0.1 | 0.1 | 0.1 | 0.1 | 0.1 |
| L-Methionine | 0.15 | 0.15 | 0.15 | 0.15 | 0.15 | 0.15 | 0.15 |
| EDTA disodium dehydrate | 0.015 | 0.015 | 0.015 | 0.015 | 0.015 | 0.015 | 0.015 |
| Water | 4 | 4 | 4 | 4 | 4 | 4 | 4 |

TABLE 3-continued

Glucagon Solution Formulation Compositions (% w/w)

| Component | F-573 | F-575 | F-590 | F-609 | F-618 | F-621 | F-648 |
|---|---|---|---|---|---|---|---|
| Sodium acetate | 0 | 0 | 1 | 1 | 0 | 0 | 0 |
| Sodium chloride | 0 | 0 | 0 | 0 | 0 | 1 | 1 |
| Calcium chloride | 0 | 0 | 0 | 0 | 2 | 1 | 1 |
| Ethanol | 15 | 15 | 15 | 15 | 15 | 15 | 15 |
| Glycerol | 0 | 30 | 0 | 30 | 30 | 30 | 0 |
| PEG 400 | | | | | | | 30 |
| Propylene glycol | qs ad to 100 | | | | | | |
| HCl | Adjust to pH 3.4 | | | | | | |

One process to prepare the glucagon solutions of the present invention is provided below:

1. Weigh out and mix edetate disodium dihydrate (EDTA), L-methionine, HCl and water to obtain Solution #1.
2. Weigh out and mix ethanol, propylene glycol, and glycerol to obtain Solution #2.
3. Weigh out glucagon.
4. Add glucagon to Solution #1 and mix well to dissolve to form Solution #3.
5. Add additional HCl to Solution #3 and mix well to obtain a clear solution (Solution #4).
6. Add a stabilizing salt (sodium acetate, sodium chloride or calcium chloride) to Solution #4 and mix well to obtain Solution #5.
7. Add Solution #2 to Solution #5 and mix well.
8. Adjust to the target pH using HCl or NaOH to obtain the final solution.
9. Pass final solution through a 0.2-micron filter.
10. Fill the filtered solution into glass vials. Crimp-seal the vials with rubber closures.

Alternatively, a glucagon solution of the present invention can be prepared by the following process:

1. Weigh out and mix all components except glucagon to obtain Solution #1.
2. Adjust pH to near the target using HCl to obtain Solution #2.
3. Pass Solution #2 through a filter as needed to remove any undissolved solids.
4. Weigh out glucagon and add glucagon to (filtered) Solution #2 and mix well to dissolve.
5. Adjust pH to the target using HCl or NaOH to obtain the final solution.
6. Pass final solution through a 0.2-micron filter.
7. Fill the filtered solution into glass vials. Crimp-seal the vials with rubber closures.

Example 5 Methods for Glucagon Stability Testing and Stability Specifications

An HPLC method for the determination of glucagon ASSAY and IMPURITIES is provided in the USP 36 Monographs for "Glucagon" and "Glucagon for Injection". This USP HPLC method was used to determine glucagon ASSAY and IMPURITIES and evaluate glucagon chemical stability in glucagon solution formulations of the present invention. The HPLC conditions are listed in the TABLE 5 below:

TABLE 5

HPLC conditions for glucagon solution formulations

| Column | C18 column, 15 cm × 3.0 mm i.d. |
|---|---|
| Mobile phase Solution | (1) Mobile phase A (MPA) Dissolve 32.6 g of $KH_2PO_4$ in 1500 mL of water, adjust with $H_3PO_4$ (85%, HPLC grade,) to a pH of 2.70 ± 0.05 (need 3-4 mL 85% $H_3PO_4$), add DI-water to 1600 mL, add 400 mL of acetonitrile, and degas. (2) Mobile phase B (MPB) Acetonitrile:DI-water = 40:60, degas. |
| Column Temp. | 45° C. |
| Sample Temp. | 5° C. |
| Flow rate | 0.5 mL/min |
| Wavelength | 214 nm |

| | Time | MPA (%) | MPB (%) |
|---|---|---|---|
| Gradient | 0 | 59 | 41 |
| | 25 | 59 | 41 |
| | 29 | 12 | 88 |
| | 30 | 12 | 88 |
| | 31 | 59 | 41 |
| | 70 | 59 | 41 |

Figure 2:
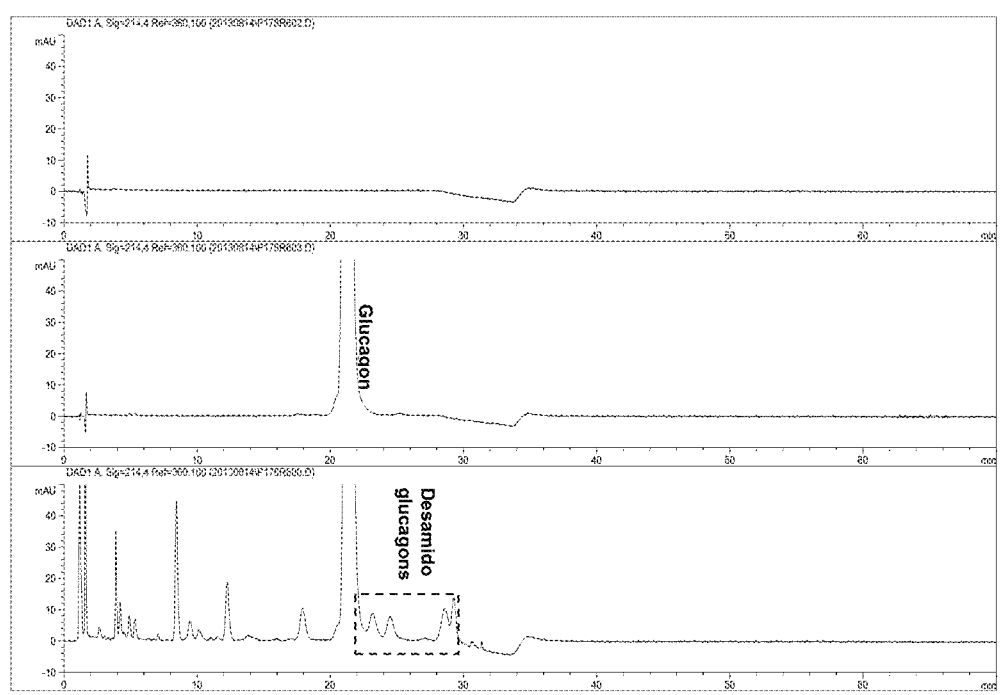
FIG. 2—illustrates representative HPLC chromatograms of an HPLC sample diluent/blank (upper), freshly prepared (middle) and a degraded (bottom) glucagon obtained using the USP HPLC method as described in Example 5.

This method allows the determination of glucagon concentration (ASSAY) and IMPURITIES. The ASSAY value is proportional to the peak area of glucagon and the IMPURITY is calculated based on the peak area percentage of the glucagon-related impurity peaks over the total peaks. The glucagon deamidation product peaks (desamido glucagons) are also calculated (FIG. 2). The relative stability of glucagon in the solution formulations of this invention can be determined by comparing the loss rate of ASSAY, the increase in total IMPURITIES or the increase in desamido glucagons formed under the same storage condition.

Example 6 Improvements to Glucagon Stability in the Solution Formulations of the Present Invention by Adding Stabilizing-Salts The following solution formulations were prepared using the same method described in Example 4 and tested and compared for glucagon stability using the method described in Example 5. Each formulation was stored at 40° C.×7 days to allow the glucagon to degrade. The relative stability for each formulation, as expressed in loss rate of ASSAY (μg/mL/day), the increase in total IMPURITIES (% peak area) and the increase in desamido glucagons (% peak area) are summarized in TABLE 6.

TABLE 6

Effect of stabilizing-salts on glucagon stability

| Formulation | Loss Rate of ASSAY (μg/mL/day) | Total IMPURITIES (% peak area) | Desamido glucagons (% peak area) |
|---|---|---|---|
| F-573* | 7.94 | 6.24 | 2.95 |
| F-590 (=F-573 + 1% sodium acetate) | 5.72 | 4.71 | 2.11 |
| F-619 (=F-573 + 0.5% sodium chloride) | 4.57 | 4.04 | 1.65 |
| F-620 (=F-573 + 1% sodium chloride) | 3.26 | 4.39 | 1.75 |
| F-575* | 11.80 | 4.21 | 1.83 |
| F-613 (=F-575 + 0.5% sodium acetate) | 7.77 | 3.78 | 1.52 |
| F-609 (=F-575 + 1% sodium acetate) | 7.60 | 3.73 | 1.51 |
| F-615 (=F-575 + 0.23% zinc acetate) | 6.85 | 4.00 | 1.99 |
| F-616 (=F-575 + 0.13% magnesium chloride) | 8.90 | 4.21 | 1.84 |
| F-617 (=F-575 + 1.1% calcium chloride) | 4.66 | 3.78 | 1.49 |
| F-618 (=F-575 + 2.0% calcium chloride) | 4.55 | 3.25 | 1.36 |

*See Example 4 for composition information on F-573 and F-575

The data shows that the addition of stabilizing-salts decreased the Loss Rate of ASSAY and formation of IMPURITIES and desamido glucagons in the solution formulations of the present invention.

Figure 3:
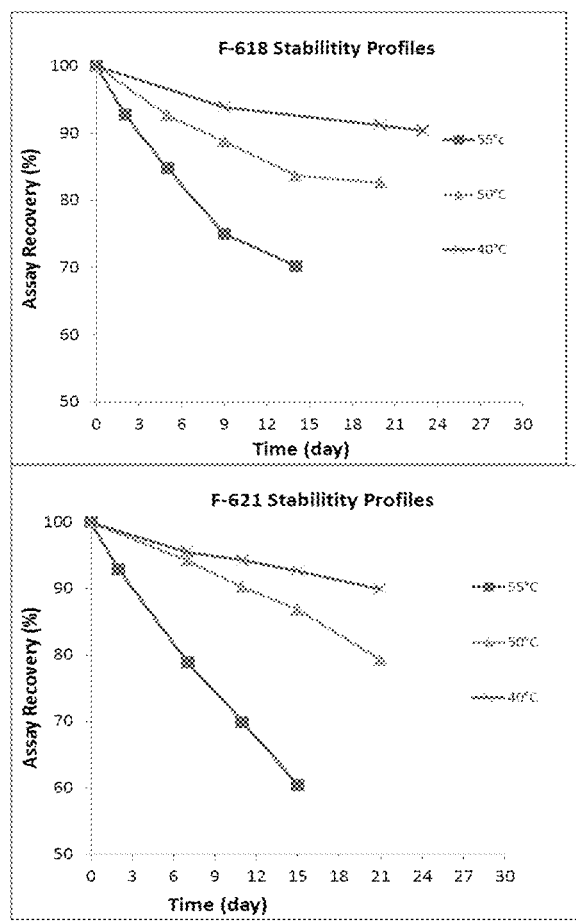
FIG. 3—shows glucagon degradation measured at various temperatures and used to construct an Arrhenius equation for determining predicted shelf life for the solution formulations of the present invention.

Example 7 Arrhenius Study of Glucagon Degradation Rates and Estimate of Shelf Life of Glucagon Solutions of the Present Invention Two glucagon solution formulations (F-618 and F-621, the composition and method of making previously described Example 4) were evaluated for their chemical stability and an estimate for their shelf life was calculated using the Arrhenius equation. F-618 and F-621 were stored at 40° C., 50° C. and 55° C. and tested for glucagon ASSAY using the HPLC method described in Example 5. At each temperature, the ASSAY values measured were used to calculate glucagon degradation rates (FIG. 3), and the rate values used to establish an Arrhenius equation, which was then used to calculate or predict the shelf-life at 5° C. (refrigeration) and 25° C. (room temperature) (TABLE 7). To define shelf life, the USP requirement of no less than 65% of ASSAY at the time of expiration was used.

TABLE 7

Estimated Shelf-life for glucagon solutions (F-618 and F-621)

| | Experimental Data | | | | Estimated Shelf Life based on 65% ASSAY Remaining (Months) |
|---|---|---|---|---|---|
| ID | Temp. (° C.) | (1000K)/T | K (rate constant) | Ln K | |
| F-618 | 5 | 3.597 | 0.00003442 | −10.28 | 417 |
| | 25 | 3.356 | 0.00058760 | −7.44 | 24 |
| | 40 | 3.195 | 0.00420996 | −5.47 | |
| | 50 | 3.096 | 0.00973681 | −4.63 | |
| | 55 | 3.049 | 0.02556790 | −3.67 | |
| F-621 | 5 | 3.597 | 0.00003184 | −10.35 | 451 |
| | 25 | 3.356 | 0.00061709 | −7.39 | 23 |
| | 40 | 3.195 | 0.00429086 | −5.31 | |
| | 50 | 3.096 | 0.01093061 | −4.52 | |
| | 55 | 3.049 | 0.03307767 | −3.41 | |

Arrhenius Parameters: $E_a$ = 102.1 KJ ∎ mol$^{-1}$; A = 4.84 × $10^{14}$ L moL$^{-1}$ s$^{-1}$ This study indicates that the glucagon solutions of the present invention have a predicted shelf life of more than 24 months at 5° C. or more than 12 months at 25° C. The formulations can be deemed chemically-stable as they were able to retain no less than 65% of the initial glucagon concentration and meet the USP ASSAY requirement for Glucagon for Injection after (1) 7 days at or near body temperature (30-40° C.), (2) after storage under a stressing condition that is equivalent to 24 months at 5° C., or (3) after storage under a stressing condition that is equivalent to 12 months at 25° C.

Example 8 Effect of Water Content on Glucagon Stability

The aim of this study was to investigate the effect of water content on glucagon stability in F-573 (a composition previously described in Example 4). F-573 formulation solutions with water content varying from 0% to 20% were prepared as shown below:
(1) Mix EDTA, methionine, HCl and water to form Solution #1.
(2) Add glucagon to Solution #1 to form Solution #2.
(3) Remove water by freeze drying to form dry solid.
(4) Add a combination of anhydrous ethanol and propylene glycol to the dry solid and mix to dissolve the solid.
(5) Adjust pH to about 3.3 using HCl.
(6) Add water to a target content level (from 0% to 20% of the final weight).
(7) Add propylene glycol to final weight and mix to obtain the final solution.
(8) Divide and seal the final solution into glass vials.
(9) Place vials at 25° C., 30° C. and 40° C.
(10) Test the vials over time for glucagon stability using the HPLC method described in Example 5.

TABLE 8

Effect of water level on glucagon stability

| | Glucagon Degradation (40° C. × 6 days) | |
|---|---|---|
| Water content (%) | Loss Rate of ASSAY (μg/mL/day) | Desamido glucagons (% peak area) |
| 0 | 10.92 | 4.09 |
| 1 | 9.36 | 3.20 |
| 2 | 8.93 | 3.57 |
| 3 | 7.18 | 3.56 |
| 4 | 8.06 | 3.40 |
| 5 | 9.02 | 3.60 |
| 10 | 11.14 | 4.12 |
| 15 | 11.80 | 4.07 |
| 20 | 11.09 | 4.68 |

Based on the data, the water content in a solution formulation of the present invention can vary between 0% and 20%, preferably 1 to 5% or more preferably 2 to 5%.

Example 9 Effect of pH on Glucagon Stability

A solution composition of the present invention, F-590 (composition and method of making described earlier in Example 4), was prepared and divided into several portions. For each portion the pH was adjusted with HCl to a different pH between pH 2.8 and 6.9. The solutions were then filled and sealed in glass vials, placed at 25° C. and 40° C. and analyzed for glucagon stability over time using the HPLC method described in Example 5. The stability testing results are shown in TABLE 8.

TABLE 8

Effect of pH on F-590 stability

Chemical stability

| | 40° C. × 6 days | | | 25° C. × 24 days | | |
|---|---|---|---|---|---|---|
| pH | Loss Rate of ASSAY (µg/mL/day) | Desamido glucagons (% peak area) | Total IMPURITIES (% peak area) | Loss Rate of ASSAY (µg/mL/day) | Desamido glucagons (% peak area) | Total IMPURITIES (% peak area) |
| 2.8 | 6.72 | 2.09 | 5.31 | 1.98 | 1.68 | 5.78 |
| 3.4 | 4.22 | 1.89 | 3.40 | 0.98 | 1.58 | 4.06 |
| 4.2 | 6.39 | 2.85 | 4.69 | 1.28 | 2.20 | 4.05 |
| 5.0 | Gel | 7.54 | 10.30 | 6.76 | 4.74 | 6.07 |
| 6.0 | 65.3 | 7.55 | 9.72 | 2.18 | 6.04 | 7.68 |
| 6.9 | 11.5 | 6.73 | 8.11 | Not tested | Not tested | Not tested |

The glucagon stability data indicate that pH for solution formulations of the present invention is preferred at no higher than 5, and more preferably between 2.8 and 4.2.

Example 10 Improvements to Glucagon Stability by Other Additives

The aim of this study was to determine if, in addition to stabilizing-salts, other additives could also improve glucagon stability in a non-gelling solution formulation of the present composition. The additives evaluated in this study included (1) amino acids (glycine, proline, aspartic acid, asparagine, glutamine, glutamic acid, proline, histidine, lysine); (2) phospholipids (egg lecithin, soy lecithin, and hydrogenated soy lecithin); (3) carbohydrates and sugar alcohols (lactose, mannitol, sorbitol); (4) salts (ammonium acetate, sodium acetate); (5) hydrophilic polymers (sodium carboxylmethyl cellulose, gelatin); (6) preservatives (benzyl alcohol, benzyl benzoate); (7) complexing agents (zinc chloride, gamma-cyclodextrin, hydroxyproply-beta-cyclodextrin); and (8) oil (medium chain triglyceride). Each additive was individually added into the F-573 solution (described in Example 4). The rate of glucagon degradation was measured for each formulation using the HPLC method described in Example 5.

Surprisingly, it was found that the salts such as sodium acetate significantly improved the glucagon chemical stability in F-573, whereas the other additives tested did not.

Example 10 Glucagon Pharmacodynamic Study

The bioactivity of glucagon in the glucagon solution formulations of the present invention was confirmed by comparing the pharmacodynamics of glucagon (i.e., blood glucose versus time) of F-618 and F-621 (Example 4) with the Glucagon Emergency Kit (Eli Lilly) following intramuscular injection in rats.

To measure the pharmacodynamics of glucagon, male Sprague-Dawley (SD) rats were administered 0.1 mg/kg glucagon in a test formulation intramuscularly. The rat dose was a calculated equivalent to the human hypoglycemia rescue dose (1 mg/60 kg human) using a proportionality based on body surface area (Reagan-Shaw, S., et al. 2008. The FASEB Journal 22(3): 659-661). A small blood sample (10-20 µL) was collected from the tip of the tail at 0, 10, 20, 30, 45, 60 and 90 minutes after dosing. Blood glucose concentrations were determined using a glucometer.

Figure 4:
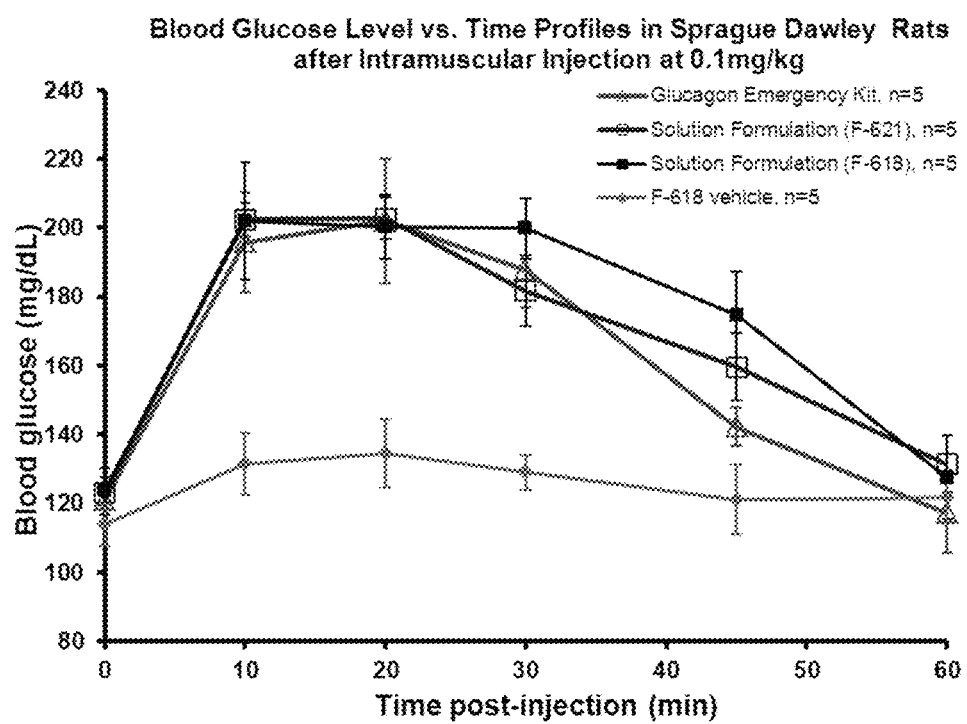
FIG. 4—shows pharmacodynamic profiles for two glucagon compositions of the present invention (F-618 and F-621) compared to that for the Glucagon Emergency Kit (Eli Lilly). Both F-618 and F-621 produced the maximum blood glucose level within 20 min and are fast-acting.

Representative pharmacodynamic (PD) profiles of F-618, F-621 and the Glucagon Emergency Kit are shown in FIG. 4. This study demonstrated that the glucagon solution formulations of the present invention were fast-acting, elevating blood glucose levels quickly and reaching a maximum level within 20 minutes. The PD profiles of the glucagon solution formulations of the present invention were similar to that for the Glucagon Emergency Kit.

Example 11 Pump-ability Evaluation

This purpose of this study was to determine the accuracy of delivering a solution composition of the present invention using an insulin pump. A Medtronic MiniMed Paradigm 722 Insulin Pump (Ref: MMT-722NAS) was equipped with an infusion set (Medtronic Quick-Set Paradigm Infusion Set (Ref: MMT-396)). The pump reservoir (Medtronic Paradigm Reservoir (3 mL) (Ref: MMT-332A)) was filled with water as a control or with a glucagon solution of the present invention (F-621 described earlier in Example 4). After the pump was initially primed, the "Easy Bolus" function was used to inject a set desired volume. The actual volume ejected from the infusion set was weighed. The delivered volume accuracy was determined by comparing the set volume and the actual delivered volume (Table below). The data showed that the F-621 solution of the present invention can be accurately delivered by an insulin pump.

| Set volume (microliter) | Actual volume delivered (microliter *) |
|---|---|
| 20 | 21.27 |
| 40 | 40.98 |
| 60 | 61.48 |
| 80 | 82.08 |
| 100 | 100.21 |

* Density of F-621 is about 1 g/mL at RT

Example 12 Biological Activity of Glucagon Formulations of the Present Invention The biological activity of a formulation of the present invention was tested in two female Sinclair swine (50-60 kg). The animals were sedated and octreotide-infused (2.7-3.6 mcg/kg/hr) during each study. The interval between each injection was at least one week. At time zero a bolus of glucagon was injected intramuscularly in the rear flank (8 mcg/kg). 2 mL venous blood samples were collected during the study at the following times (minutes): −10, −5, 0, 5, 10, 15, 20, 30, 45, 60, 75, 90, 105, 120. Blood glucose determinations were performed with a Hemocue 201 analyzer immediately upon collection. For plasma glucagon, venous blood samples were allowed to clot then centrifuged to collect plasma and stored at −20° C. prior to analysis using a glucagon RIA kit (Linco, Cat# GL-32K). PK analysis to obtain standard PK parameters such as AUC, t½, Tmax, Cmax, Clearance etc. were determined with the use of pharmacokinetic analysis software.

Figure 5:
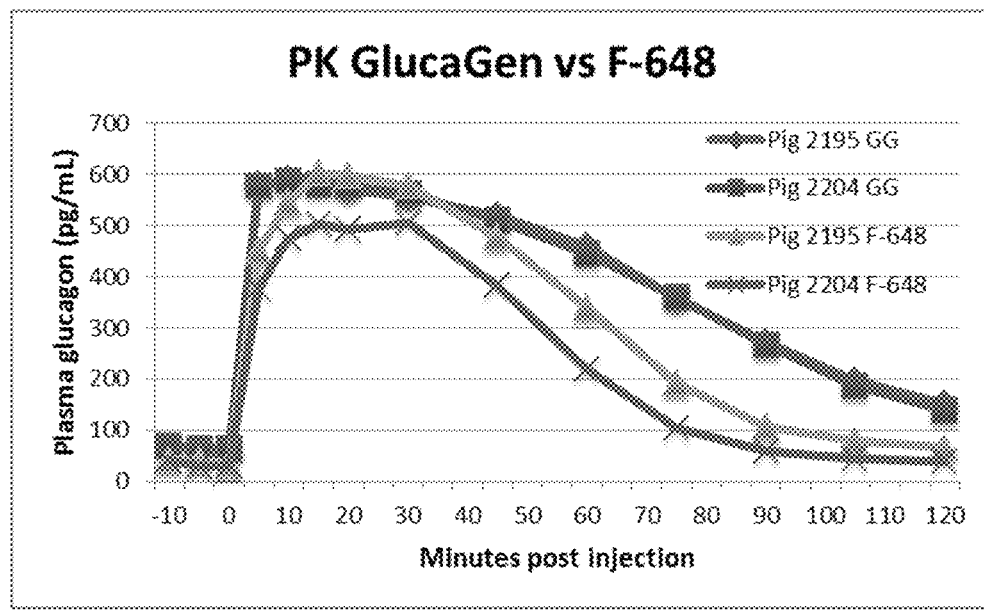
FIG. 5—shows pharmacokinetic (PK) (top) and pharmacodynamic (PD) (bottom) profiles for F-648, a formulation of the present invention. F-648 is fast acting and produces a rapidblood glucose elevation comparable to the Glucagon Emergency Kit (GlucaGen or GG).
Figure 5:
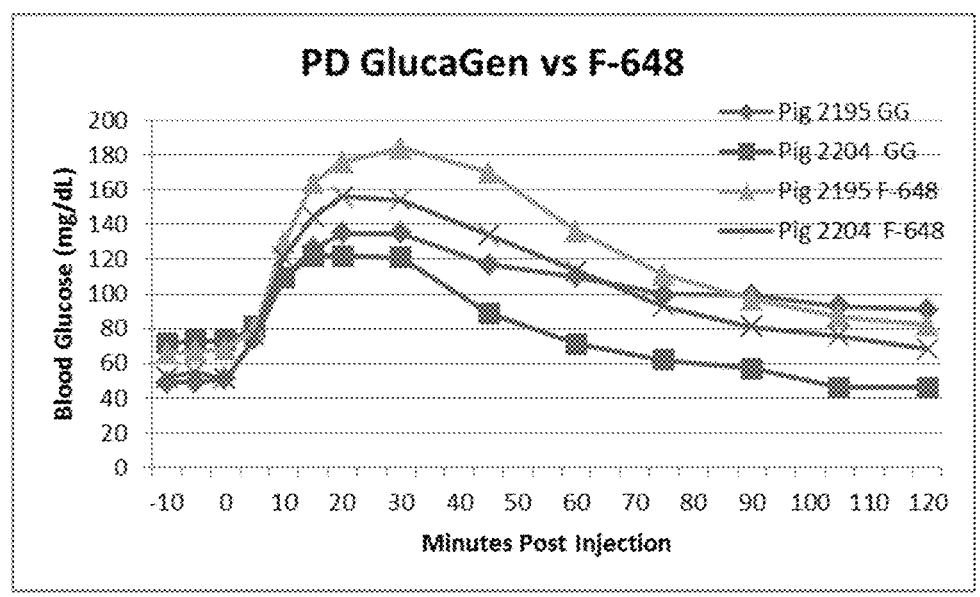

FIG. 5. (Top) shows the individual pharmacokinetic (PK) profiles produced in Sinclair pigs by a commercial glucagon (GlucaGen (Novo Nordisk A/S)) and a glucagon formulation from the present invention (F-648). The dose for each IM injection was 0.8 mcg glucagon/kg. Both GlucaGen and F-648 produced essentially identical rapid elevations and maximum concentrations (Cmax) of plasma glucagon.

FIG. 5 (Bottom) shows the individual pharmacodynamic (PD) profiles produced in Sinclair pigs by a commercial glucagon (GlucaGen (Novo Nordisk A/S)) and a glucagon formulation from the present invention (F-648). The dose for each IM injection was 0.8 mcg/kg. Both test articles induced a rapid rate of blood glucose elevation. However, the maximum blood glucose elevation produced by F-648 was greater than GlucaGen, indicating that F-648 was at least as potent as GlucaGen in raising blood glucose.

No injection site reactions nor were any whole animal adverse reactions observed in response to intramuscular injections of GlucaGen or F-648, indicating that F-648 was as safe as the reference listed drug in these respects.

Example 13 Long-term Stability of Glucagon Solutions of the Present Invention

Two formulations of the present invention, F-621 and F-648, were prepared and filled into type 2 glass vials. The vials were stored upright at −20, 2-8, 25, 30 and 40° C. The glucagon concentration and purity were determined using USP HPLC methods. The stability data from up to 24 months storage are shown TABLES 9 and 10 below. Both formulations are liquid, ready-to-use, non-gelling, injectable, chemically-stable and pump-able after 24 months storage at 2-8° C., 12 months storage at 25° C., 6 months storage at 30° C. and 3 months storage at 40° C.

TABLE 9

Stability of F-621

| Test | Storage Temperature (° C.) | Day 0 | 1M | 3M | 6M | 9.5M | 14M | 18M | 24M |
|---|---|---|---|---|---|---|---|---|---|
| Appearance | 2-8 | Liquid, clear, colorless, non-gelling, injectable & pumpable | Same | Same | Same | Same | Same | Same | Same |
|  | 25 |  | Same | Same | Same | Same | Same | Same | Same |
|  | 30 |  | Same | Same | Same | Same | Same | Same | Same |
|  | 40 |  | Same | Same | Same | Same | Same | Same | Same |
| pH | 2-8 | 3.5 | — | — | 3.4 | 3.4 | — | 3.3 | 3.5 |
|  | 25 |  | 3.6 | — | 3.4 | 3.5 | 3.5 | 3.4 | — |
|  | 30 |  | 3.6 | — | 3.5 | 3.4 | — | — | — |
|  | 40 |  | 3.6 | — | 3.6 | — | — | — | — |
| Glucagon assay (mg/mL)* | 2-8 | 1.11 | — | 1.09 | 1.10 | 1.06 | 1.08 | 1.07 | 1.00 |
|  | 25 |  | 1.08 | 1.01 | 0.93 | 0.86 | 0.77 | 0.71 | — |
|  | 30 |  | 1.06 | 0.94 | 0.82 | 0.68 | — | — | — |
|  | 40 |  | 0.95 | 0.70 | 0.45 | — | — | — | — |
| Assay recovery (% over the Day 0 value) | 2-8 | 100 | — | 99.1 | 99.1 | 95.7 | 97.6 | 96.5 | 90.4 |
|  | 25 |  | 97.8 | 91.7 | 84.3 | 77.7 | 69.1 | 64.0 | — |
|  | 30 |  | 95.8 | 86.5 | 74.0 | 61.3 | — | — | — |
|  | 40 |  | 85.4 | 64.4 | 40.4 | — | — | — | — |
| Glucagon purity (% by peak area) | 2-8 | 98.7 | — | 97.8 | 96.6 | 96.5 | 93.8 | 94.7 | 96.0 |
|  | 25 |  | 96.5 | 90.9 | 83.7 | 77.1 | 77.8 | 70.2 | — |
|  | 30 |  | 94.6 | 85.6 | 74.4 | 66.7 | — | — | — |
|  | 40 |  | 86.2 | 68.2 | 44.9 | — | — | — | — |

TABLE 10

Stability of F-648

| Test | Storage Temperature (° C.) | Day 0 | 1M | 3M | 6M | 12M | 20M | 24M |
|---|---|---|---|---|---|---|---|---|
| Appearance | 2-8 | Liquid, clear, colorless, non-gelling, injectable & pumpable | Same | Same | Same | Same | Same | Same |
|  | 25 |  | Same | Same | Same | Same | Same | Same |
|  | 30 |  | Same | Same | Same | Same | — | — |
|  | 40 |  | Same | Same | Same | Same | — | — |
| pH | 2-8 | 3.1 | — | 3.1 | 2.9 | 3.4 | 3.3 | 3.3 |
|  | 25 |  | 3.0 | 3.1 | 2.8 | 3.3 | — | — |
|  | 30 |  | 3.0 | 3.1 | — | — | — | — |
|  | 40 |  | 3.0 | 3.1 | — | — | — | — |

TABLE 10-continued

Stability of F-648

| Test | Storage Temperature (° C.) | Day 0 | 1M | 3M | 6M | 12M | 20M | 24M |
|---|---|---|---|---|---|---|---|---|
| Glucagon assay (mg/mL)* | 2-8 | 0.88 | — | 0.87 | 0.86 | 0.86 | 0.76 | 0.80 |
|  | 25 |  | 0.85 | 0.80 | 0.75 | 0.59 | — | — |
|  | 30 |  | 0.84 | 0.73 | 0.60 | — | — | — |
|  | 40 |  | 0.75 | 0.53 | 0.34 | — | — | — |
| Assay recovery (% over Day 0 value) | 2-8 | 100 | — | 98.4 | 97.4 | 95.9 | 86.4 | 91.0 |
|  | 25 |  | 96.1 | 91.2 | 85.2 | 67.3 | — | — |
|  | 30 |  | 95.7 | 82.8 | 67.7 | — | — | — |
|  | 40 |  | 85.1 | 60.4 | 38.5 | — | — | — |
| Purity (% by peak area) | 2-8 | 98.6 | — | 97.4 | 96.9 | 91.4 | 87.8 | 84.7 |
|  | 25 |  | 93.5 | 90.6 | 85.2 | 68.7 | — | — |
|  | 30 |  | 91.8 | 84.3 | — | — | — | — |
|  | 40 |  | 81.0 | 67.0 | — | — | — | — |

Modifications and variations of the present invention will be obvious to those skilled in the art from the foregoing detailed description and are intended to fall within the scope of the following claims. The teachings of all references cited herein are specifically incorporated by reference.

The invention claimed is:

1. A ready-to-use, non-gelling, clear and one-phase solution composition, the composition comprising: glucagon having a concentration between 0.05 mg/mL and 5 mg/mL, water having a concentration between 3% and 5% w/v, an anti-gelling polyol comprising a combination of a propylene glycol and polyethylene glycol having a concentration between 60% and 97% w/v, an acid in sufficient quantity to adjust pH of the composition to a pH between 2 and 4, a stabilizing-salt selected from the group consisting of sodium chloride, calcium chloride, sodium acetate or a combination thereof, having a concentration between 0.5% and 3% w/v, an antioxidant selected from the group consisting of methionine, EDTA or a combination thereof having a concentration between 0.01% and 1% w/v, and optionally ethanol as a viscosity-reducer, wherein the clear and one-phase composition is free from cationic surfactants or a phospholipid and retains no less than 65% of the initial glucagon concentration after 24-month storage at 2-8° C.

2. The composition according to claim 1, wherein the glucagon is derived from an animal source, made synthetically or produced by DNA recombinant technology.

3. The composition according to claim 1, wherein the acid is selected from the group consisting of hydrochloric acid, phosphoric acid, methanesulfonic acid, sulfuric acid, acetic acid, lactic acid, tartaric acid, citric acid, propionic acid and a mixture thereof.

4. The composition according to claim 1 wherein viscosity reducer is at a concentration between 1 to 25% by weight of the total composition.

5. The composition according to claim 1, wherein said composition provides a fast-acting glucagon efficacy by elevating blood glucose following a subcutaneous, intramuscular or intravenous injection using a syringe, pen-injector, auto-injector, unit dose auto-injector or infusion pump, or other injection device.

6. A method of treatment of hypoglycemia, hyperinsulinemia or for reducing intestinal motility during radiologic examination of the stomach, duodenum, small bowel, and colon when diminished intestinal motility in a human or animal subject, said method comprising administering to said subject an effective amount of a solution as claimed in claim 1.

7. A method for preparing the composition as claimed in claim 1, said method comprising (1) combining, mixing and dissolving the anti-gelling polyol comprising a combination of a propylene glycol and polyethylene glycol having a concentration between 60% and 97% w/v;

the stabilizing-salt selected from the group consisting of sodium chloride, calcium chloride, sodium acetate or a combination thereof, having a concentration between 0.5% and 3% w/v;

the antioxidant selected from the group consisting of methionine, EDTA or a combination thereof having a concentration between 0.01% and 1% w/v;

water having a concentration between 3% and 5% w/v; and optionally ethanol as a viscosity-reducer;

adding an acid in sufficient quantity to a pH between 2 and 4; and including glucagon having a concentration between 0.05 mg/mL and 5 mg/mL to form a clear solution, (2) passing the solution through a filter and (3) filling the filtered solution into a vial, syringe, insulin pump cartridge, an auto-injector, a unit dose auto-injector or other injection device.

* * * * *

SEQUENCE LISTING

```
<160> NUMBER OF SEQ ID NOS: 1

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```